United States Patent [19]

Edwards

[11] 4,068,000
[45] Jan. 10, 1978

[54] METHOD FOR CONTROLLING MITES
[75] Inventor: Laroy H. Edwards, Napa, Calif.
[73] Assignee: Chevron Research Company, San Francisco, Calif.
[21] Appl. No.: 714,462
[22] Filed: Aug. 16, 1976
[51] Int. Cl.² .................. A01N 9/16; C07C 143/72; C07C 143/84
[52] U.S. Cl. .................. 424/321; 260/556 A; 260/556 AR
[58] Field of Search .................. 424/321; 260/556 A, 260/556 AR

[56] References Cited

U.S. PATENT DOCUMENTS

| | | | |
|---|---|---|---|
| 2,779,788 | 1/1957 | Gysin et al. | 424/321 |
| 2,779,941 | 1/1957 | Gysin et al. | 424/321 |
| 3,178,447 | 4/1965 | Kohn | 260/309.5 |
| 3,678,017 | 7/1972 | Shelton et al. | 260/556 A |
| 3,703,500 | 11/1972 | Nast et al. | 260/556 A |
| 3,925,555 | 12/1975 | Okuda et al. | 424/321 |

Primary Examiner—Albert T. Meyers
Assistant Examiner—D. W. Robinson
Attorney, Agent, or Firm—Dix A. Newell; Raymond Owyang

[57] ABSTRACT

Mite eggs are killed by applying thereto N-tetrachloroethylthio-substituted halomethanesulfonamides of the formula

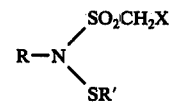

wherein R is alkyl, cycloalkyl, aryl, X is fluoro, chloro, bromo or iodo and R' is tetrachloroethyl.

10 Claims, No Drawings

METHOD FOR CONTROLLING MITES

BACKGROUND OF THE INVENTION

U.S. Pat. No. 3,178,447, issued to G. K. Kohn on Apr. 13, 1965, discloses the fungicidal activity of N-polyhaloethylthio-substituted aryl- and alkanesulfonamides.

U.S. Pat. No. 2,779,788, issued to H. Gysin et al on Jan. 29, 1957, discloses fungicidal N-trichloromethylthio-substituted chloromethanesulfonamides.

U.S. Pat. No. 3,925,555, issued to I. Okuda et al on Dec. 9, 1975, discloses the control of mites with chloromethanesulfonamides.

DESCRIPTION OF THE INVENTION

The mite ovicidal compounds of the invention are represented by the formula

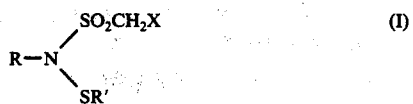 (I)

wherein R is alkyl of 1 to 8 carbon atoms, cycloalkyl of 5 to 8 carbon atoms substituted with up to 2 alkyl of 1 to 3 carbon atoms, phenyl substituted with up to 2 fluoro, chloro, bromo, iodo or alkyl of 1 to 4 carbon atoms; X is fluoro, chloro, bromo or iodo and R' is tetrachloroethyl.

Representative R groups include alkyl such as methyl, ethyl, isopropyl, sec-butyl and hexyl; cycloalkyl and alkylcycloalkyl such as cyclopentyl, 2-methylcycloalkyl, 3-methylcyclohexyl, 3,5-dimethylcycloheptyl and cyclooctyl; and aryl groups such as phenyl, 2-fluorophenyl, 3-chlorophenyl, 4-bromophenyl, 4-iodophenyl, 4-methylphenyl and 2-chloro-4-methylphenyl. Tetrachloroethyl R' groups are 1,1,2,2-tetrachloroethyl and 1,2,2,2-tetrachloroethyl.

Preferred R groups are alkyl, especially alkyl of 1 to 4 carbon atoms and cycloalkyl of 5 to 6 carbon atoms substituted with up to 1 alkyl of 1 to 3 carbon atoms. The preferred X groups are chloro or bromo. The preferred R' group is 1,1,2,2-tetrachloroethyl.

Representative compounds of formula (I) include N-cyclopentyl-N-(1,1,2,2-tetrachloroethylthio)-chloromethanesulfonamide, N-cycloheptyl-N-(1,1,2,2,-tetrachloroethylthio)-bromomethanesulfonamide, N-(2-fluorophenyl)-N-(1,1,2,2-tetrachloroethylthio)-iodomethanesulfonamide, N-(4-chlorophenyl)-1,1,2,2-tetrachloroethylthio)-bromomethanesulfonamide, N-(3-iodophenyl)-N-(1,1,2,2-tetrachloroethylthio)-iodomethanesulfonamide, N-cyclohexyl-N-(1,2,2,2-tetrachloroethylthio)-bromomethanesulfonamide, N-phenyl-N-(1,2,2,2-tetrachloroethylthio)-chloromethanesulfonamide, N-isopropyl-N-(1,2,2,2,-tetrachloroethylthio)-fluoromethanesulfonamide, and N-(2,4-dichlorophenyl)-N-(1,2,2,2-tetrachloroethylthio)-chloromethanesulfonamide.

The compounds of the invention are prepared by sulfenylating a sulfonamide of the formula R NHSO₂CH₂X (II), wherein R and X have same significance as previously defined, with a tetrachloroethylsulfenyl halide, e.g., 1,1,2,2-tetrachloroethylsulfenyl chloride or 1,2,2,2-tetrachloroethylsulfenyl chloride. The sulfenylation reaction is conducted by reacting substantially equimolar quantities of the sulfonamide (II) and the sulfenyl halide in the liquid phase in the presence of a base. Suitable bases are organic amines such as pyridine compounds, e.g., pyridine or alpha-picoline, and lower trialkylamines, e.g., triethylamine or tributylamine, and inorganic alkali metal hydroxides, e.g., sodium hydroxide or potassium hydroxide. Generally, at least one mol of base is employed for each mol of tetrachloroethylsulfenyl halide. The reaction is normally conducted in an inert liquid diluent, e.g., organic solvents such as chlorinated hydrocarbons.

Preferably, the reaction is conducted in the presence of catalytic amounts of a quaternary ammonium salt. Generally, amounts of quaternary ammonium salt per mol of the sulfenyl halide reactant vary from about 0.01 to 0.3, although amounts from 0.05 to 0.2 mol per mol of the sulfenyl halide are preferred. Suitable quaternary ammonium salts are tetraalkylammonium halides wherein the alkyl has 1 to 6 carbon atoms and the halide is fluoro, chloro, bromo or iodo, e.g., tetramethaneammonium chloride or tetrabutylammonium bromide.

The sulfenylation reaction is conducted at a temperature of 0° C to the boiling point of the diluent, although temperatures between 0° C and 100° C are preferred. The reaction is conducted at or above atmospheric pressure. The reaction time will, of course, vary depending on the reaction temperature and the particular reactants employed. Generally, the reaction is completed within one-half to 24 hours. The product (I) is isolated and purified by conventional procedures such as extraction, filtration, crystallization and chromatography.

The compounds of the invention have been found to be useful and effective for the killing of mite eggs. Some compounds of the invention are also useful and effective for the killing of mites. The compounds of the invention also have excellent activity against fungi.

Any conventional techniques or methods can be employed for contacting mites or mite eggs with an effective miticidal or ovicidal amount of the compounds of the invention. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the mites or mite eggs, their environment or hosts susceptible to mite attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5–80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally coprises from 1 percent to 15 percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogenous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For application these concentrates are dispersed in water or other liquid carrier, and normally applied as a spray to the area to be treated.

The percentages by weight of the toxicant may vary according to the manner in which the composition is to be applied and the particular type of formulation, but in general comprises 0.5 to 95% of the toxicant by weight of the pesticidal composition.

The compositions may be formulated and applied with other active ingredients, including other nematocides, insecticides, fungicides, bactericides, plant growth regulators, fertilizers, etc. In applying the chemical an effective amount and concentration of the toxicants of this invention is, of course, employed.

EXAMPLES

EXAMPLE 1

Preparation of N-cyclo hexyl-N-(1,1,2,2-tetrachloro ethylthio)-bromomethanesulfonamide A 20 g (0.2 mol) sample of cyclohexylamine was added dropwise to a cooled ($-60°$ C) solution of 23.8 g (0.1 mol) bromomethanesulfenyl bromide in 200 ml dichloromethane. The reaction was then allowed to warm to about 25° C and stirred about 16 hours. The reaction mixture was then filtered, washed with water, dried over magnesium sulfate and evaporated to give 22.0 g of crude N-cyclohexyl bromomethanesulfonamide.

A 5.1 g (0.051 mol) sample of triethylamine was added dropwise to a cooled (20° C) solution of 11 g (0.043 mol) N-cyclohexyl bromomethanesulfonamide and 10.1 g (0.043 mol) 1,1,2,2-tetrachloroethylsulfenyl chloride. After the addition was completed, the reaction was stirred at ambient temperature for 2 hours and then under reflux for 2 hours. The reaction mixture was then cooled, washed with water, dried over magnesium sulfate and evaporated under reduced pressure to give the N-cyclohexyl-N-(1,1,2,2-tetrachloroethylthio)-bromomethanesulfonamide product, which after crystallization from dioxane melted at 38°–40° C. The elemental analysis for the product is tabulated in Table I under Compound No. 8.

EXAMPLE 2

Preparation of N-cyclopentyl-N (1,1,2,2-tetrachloroethylthio)-bromomethanesulfonamide A 5.76 g (0.072 mol) 50% aqueous solution of sodium hydroxide was added slowly to a solution of 8.6 g (0.036 mol) N-cyclopentyl bromomethanesulfonamide, 8.6 g (0.036 mol) 1,1,2,2-tetrachloroethylsulfenyl chloride, and about 0.1 g benzyltriethyl ammonium chloride in 200 mol dichloromethane cooled to 0° C with an ice bath. The reaction mixture was then stirred at 0° C for 2 hours, washed with water, dried over magnesium sulfate and evaporated to give a brown oil. The oil was chromatography over silica gel with dichloromethane/petroleum-ether elution to give 5.5 g (35% yield) of the product, as a grey solid, m.p. 59°–60° C. The elemental analysis for the product is tabulated in Table I under compound No. 9.

EXAMPLE 3

Mite Control Tests

Compounds of the invention were tested for the control mites and mite eggs by the following procedure.

Pinto bean leaves were invested with two spotted-mites (*Tetramuchus urticae*). The mites were then allowed to lay eggs on the leaves. After 48 hours, the leaves were dipped into a water/acetone solution containing a small amount of a nonionic surfactant and 40 ppm of the test compound. The treated leaves were then maintained at 85° F. One day after treatment, the mortality of adult mites was determined, and 7 days after treatment, the egg mortality (non-hatching eggs) was determined.

The results for the compounds found to have mite and mite egg control activity are tabulated in Table I.

TABLE I

Compound of the formula $R-N\begin{smallmatrix}SO_2CH_2X\\SR'\end{smallmatrix}$

| Compound No. | R | R' | X | Melting Point, °C | Mite Control Adult | Mite Control Eggs |
|---|---|---|---|---|---|---|
| 1 | i-$C_3H_7$ | $CCl_2CCl_2H$ | Cl | 78–80 | 0 | 22 |
| 2 | cyclohexyl | " | Cl | 73–74 | 90 | 100 |
| 3 | $CH_3$ | " | Cl | oil | 0 | 22 |
| 4 | φ | " | Cl | 91–92 | 0 | 50 |
| 5 | s-$C_4H_9$ | " | Cl | oil | 96 | 94 |
| 6 | cyclopentyl | " | Cl | 67–68 | 0 | 90 |
| 7 | 4-$CH_3$-cyclohexyl | " | Cl | 63–65 | 0 | 70 |
| 8 | cyclohexyl | " | Br | 38–40 | 0 | 99 |
| 9 | cyclopentyl | " | Br | 59–60 | 0 | 99 |
| 10 | s-$C_4H_9$ | " | Br | oil | 96 | 90 |
| 11 | 4-$CH_3$-cyclohexyl | " | Br | oil | 22 | 99 |
| 12 | cyclooctyl | " | Br | oil | 0 | 22 |
| 13 | φ | " | Br | 101–103 | 60 | 100 |
| 14 | $CH_3$ | " | Br | oil | 60 | 96 |
| 15 | n-$C_3H_7$ | " | Br | oil | 85 | 90 |
| 16 | i-$C_3H_7$ | " | Br | 75–77 | 0 | 100 |
| 17 | n-$C_4H_9$ | " | Br | oil | 0 | 100 |
| 18 | t-$C_4H_9$ | " | Br | 78–80 | 0 | 100 |
| 19 | p-tolyl | " | Br | 100–103 | 0 | 100 |
| 20 | i-$C_3H_7$ | $CCl_3$ | Cl | 78–80 | 0 | 0 |
| 21 | cyclohexyl | " | Cl | 108–109 | 22 | 0 |
| 22 | $CH_3$ | " | Cl | 7072 | 0 | 0 |
| 23 | cyclooctyl | " | Cl | oil | 0 | 0 |
| 24 | φ | " | Cl | 115–117 | 0 | 0 |
| 25 | s-$C_4H_9$ | " | Cl | 72–74 | 0 | 0 |
| 26 | cyclopentyl | " | Cl | 58–60 | 0 | 0 |
| 27 | 4-$CH_3$-cyclohexyl | " | Cl | 87–89 | 0 | 0 |
| 28 | cyclohexyl | " | Br | 110–111 | 0 | 0 |

TABLE I-continued

Compound of the formula  R—N(SO₂CH₂X)(SR')

| Compound No. | R | R' | X | Melting Point, °C | Mite Control Adult | Eggs |
|---|---|---|---|---|---|---|
| 29 | cyclopentyl | " | Br | 70–71 | 0 | 0 |
| 30 | s-C₄H₉ | " | Br | 71–72 | 0 | 0 |
| 31 | 4-CH₃-cyclohexyl | " | Br | 56–57 | 0 | 0 |
| 32 | cyclooctyl | " | Br | oil | 0 | 0 |
| 33 | φ | " | Br | 134–135 | 0 | 0 |
| 34 | p-tolyl | " | Br | 113–115 | 0 | 0 |

What is claimed is:

1. A compound of the formula

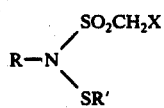

wherein R is alkyl of 1 to 8 carbon atoms, cycloalkyl of 5 to 8 carbon atoms substituted with up to 2 alkyl of 1 to 3 carbon atoms, or phenyl substituted with up to 2 fluoro, chloro, bromo, iodo or alkyl of 1 to 4 carbon atoms; X is fluoro, chloro, bromo or iodo and R' is tetrachloroethyl.

2. The compound of claim 1 wherein R' is 1,1,2,2-tetrachloroethyl.

3. The compound of claim 1 wherein R is alkyl of 1 to 4 carbon atoms.

4. The compound of claim 3 wherein R is methane, R¹ is 1,1,2,2-tetrachloroethyl, and X is chloro.

5. The compound of claim 1 wherein R is cycloalkyl of 5 to 6 carbon atoms substituted with up to 1 alkyl of 1 to 3 carbon atoms.

6. The compound of claim 1 wherein R is cyclohexyl, R' is 1,1,2,2-tetrachloroethyl and X is chloro.

7. The compound of claim 1 wherein X is chloro or bromo.

8. A method of killing mite eggs which comprises applying thereto an ovicidally effective amount of the compound defined in claim 1.

9. The method of claim 8 wherein X is bromo.

10. The method of claim 8 wherein R' is 1,1,2,2-tetrachloroethyl.

* * * * *